United States Patent
Hwang et al.

(10) Patent No.: US 10,365,160 B2
(45) Date of Patent: Jul. 30, 2019

(54) SPECTRUM MEASUREMENT APPARATUS AND METHOD, AND CALIBRATION METHOD OF SPECTRUM MEASUREMENT APPARATUS

(71) Applicant: SAMSUNG ELECTRONICS CO., LTD., Suwon-si (KR)

(72) Inventors: Hyo Sun Hwang, Seoul (KR); So Young Lee, Daejeon (KR); Jae Wook Shim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 8 days.

(21) Appl. No.: 15/881,037

(22) Filed: Jan. 26, 2018

(65) Prior Publication Data

US 2019/0041269 A1  Feb. 7, 2019

(30) Foreign Application Priority Data

Aug. 2, 2017 (KR) .................. 10-2017-0098136

(51) Int. Cl.
*G01J 3/457* (2006.01)
*G01J 3/28* (2006.01)

(52) U.S. Cl.
CPC ............ *G01J 3/457* (2013.01); *G01J 3/28* (2013.01); *G01J 3/2803* (2013.01); *G01J 2003/284* (2013.01); *G01J 2003/2866* (2013.01)

(58) Field of Classification Search
CPC ........ G01J 3/457; G01J 3/28; G01J 2003/284; G01J 3/2866
See application file for complete search history.

(56) References Cited

U.S. PATENT DOCUMENTS

| 6,816,241 | B2 | 11/2004 | Grubisic |
| 6,990,364 | B2 | 1/2006 | Ruchti et al. |
| 7,479,111 | B2 | 1/2009 | Zhang et al. |
| 9,297,749 | B2 | 3/2016 | Micheels et al. |

(Continued)

FOREIGN PATENT DOCUMENTS

| KR | 101078135 B1 | 10/2011 |
| KR | 1020170023628 A | 3/2017 |
| WO | 2010082852 A1 | 7/2010 |

OTHER PUBLICATIONS

Tai-Sheng Yeh et al. "A Low Cost LED Based Spectrometer" Journal of the Chinese Chemical Society, vol. 53, No. 5, 2006, (pp. 1067-1072).

*Primary Examiner* — Hina F Ayub
(74) *Attorney, Agent, or Firm* — Sughrue Mion, PLLC

(57) ABSTRACT

Provided is a spectrum measurement apparatus including a light source configured to emit light to a sample; a light detector configured to receive light, which is reflected or scattered from, or transmitted through the sample, and to measure an intensity of the received light, and a processor configured to reconstruct a spectrum of the sample for calibration while adjusting a value of a spectrum reconstruction parameter in response to the light detector receiving the light and measuring the intensity of the received light, and to determine an optimal value of the spectrum reconstruction parameter based on a similarity between the reconstructed spectrum of the sample for calibration and an original spectrum of the sample for calibration.

20 Claims, 13 Drawing Sheets

(56) References Cited

U.S. PATENT DOCUMENTS

2008/0118181 A1* 5/2008 Potuluri .................... G01J 3/02
382/275
2015/0045641 A1* 2/2015 Rule .................... A61B 5/7435
600/347
2017/0059409 A1 3/2017 Eom

* cited by examiner

SPECTRUM MEASUREMENT APPARATUS AND METHOD, AND CALIBRATION METHOD OF SPECTRUM MEASUREMENT APPARATUS

CROSS-REFERENCE TO RELATED APPLICATION

This application claims priority from Korean Patent Application No. 10-2017-0098136, filed on Aug. 2, 2017, in the Korean Intellectual Property Office, the disclosure of which is incorporated herein by reference by its entirety.

BACKGROUND

1. Field

Example embodiments relate generally to technology for spectrum reconstruction, and more particularly to a spectrum measurement apparatus, a spectrum measurement method, and a calibration method of the spectrum measurement apparatus.

2. Description of the Related Art

A spectrometer is an instrument which detects light reflected or scattered from, or transmitted through a sample, and analyzes the composition of the sample to determine properties of the sample, in which based on a measurement value of a light detector, the spectrometer may obtain a spectrum of the sample by using a spectrum reconstruction algorithm.

Accordingly, in order to improve the performance of the spectrometer, there is a need to optimize the spectrum reconstruction algorithm and a parameter used for the algorithm.

SUMMARY

Example embodiments provide a spectrum measurement apparatus, a spectrum measurement method, and a calibration method of the spectrum measurement apparatus.

According to an aspect of an example embodiment, there is provided a spectrum measurement apparatus including a light source configured to emit light to a sample, a light detector configured to receive light, which is reflected or scattered from, or transmitted through the sample, and to measure an intensity of the received light, and a processor configured to reconstruct a spectrum of the sample for calibration while adjusting a value of a spectrum reconstruction parameter in response to the light detector receiving the light and measuring the intensity of the received light, and to determine an optimal value of the spectrum reconstruction parameter based on a similarity between the reconstructed spectrum of the sample for calibration and an original spectrum of the sample for calibration.

The processor may be further configured to calculate the similarity between the reconstructed spectrum of the sample for calibration and the original spectrum of the sample for calibration by using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

The processor may be configured to determine, as the optimal value of the spectrum reconstruction parameter, a value of the spectrum reconstruction parameter at which the similarity between the reconstructed spectrum of the sample for calibration and the original spectrum of the sample for calibration is maximized.

The processor may be further configured to reconstruct a spectrum of the sample corresponding to the determined optimal value of the spectrum reconstruction parameter, in response to the light detector receiving the light and measuring the intensity of the received light.

The processor may be further configured to determine a system noise state, which affects spectrum reconstruction, based on a change in the similarity between the reconstructed spectrum of the sample for calibration and the original spectrum of the sample for calibration according to a change in the spectrum reconstruction parameter.

The processor may be further configured to determine the system noise state based on a number of maximum points of the change in the similarity according to the change in the spectrum reconstruction parameter.

In response to the number of the maximum points being one, the processor may be further configured to determine the system noise state to be an appropriate state, and in response to the number of the maximum points not being one, the processor may be further configured to determine the system noise state to be an inappropriate state.

In response to determination of the system noise state to be in the inappropriate state, the processor may be further configured to adjust a system parameter.

The system parameter may include at least one from among a light source parameter and a light detector parameter, wherein the light source parameter includes at least one from among an operating frequency and a duty ratio of the light source, and a size of an electric signal applied to the light source; and the light detector parameter includes at least one from among an operating frequency and an amplification gain of the light detector.

The processor may be further configured to analyze a relationship between at least one from among a change in the light source parameter and a temperature change of the light source according to the change in the light source parameter, and a noise, and a relationship between at least one from among a change in the light detector parameter and a temperature change of the light detector according to the change in the light detector parameter, and a noise, wherein based on the analysis, the processor may be further configured to adjust at least one from among the light source parameter and the light detector parameter to minimize a system noise.

According to another aspect of an example embodiment, there is provided a calibration method of a spectrum measurement apparatus, the method including emitting light to a sample for calibration, receiving light, which is reflected or scattered from, or transmitted through the sample for calibration, and measuring an intensity of the received light, in response to measuring the intensity of the received light, reconstructing a spectrum of the sample for calibration while adjusting a value of a spectrum reconstruction parameter, determining a similarity between the reconstructed spectrum of the sample for calibration and an original spectrum of the sample for calibration, and determining an optimal value of the spectrum reconstruction parameter based on the determined similarity.

The determining of the similarity may include using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

The determining of the optimal value of the spectrum reconstruction parameter may include determining, as the optimal value of the spectrum reconstruction parameter, a value of the spectrum reconstruction parameter at which the similarity between the reconstructed spectrum of the sample for calibration and the original spectrum of the sample for calibration is maximized.

The method may further include determining a system noise state, which affects spectrum reconstruction, based on a change in the similarity between the reconstructed spectrum of the sample for calibration and the original spectrum of the sample for calibration according to a change in the spectrum reconstruction parameter.

The determining of the system noise state may include determining the system noise state based on a number of maximum points of the change in the similarity according to the change in the spectrum reconstruction parameter.

The determining of the system noise state may include, in response to the number of the maximum points being one, determining the system noise state to be in an appropriate state, and in response to the number of the maximum points not being one, determining the system noise state to be in an inappropriate state.

The method may further include, in response to determination of the system noise state to be in the inappropriate state, adjusting a system parameter.

The system parameter may include at least one from among a light source parameter and a light detector parameter, wherein the light source parameter includes at least one from among an operating frequency and a duty ratio of a light source unit, and a size of an electric signal applied to the light source unit, and the light detector parameter includes at least one from among an operating frequency and an amplification gain of a light detector.

The method may further include analyzing a relationship between at least one from among a change in the light source parameter and a temperature change of the light source unit according to the change in the light source parameter, and a noise, analyzing a relationship between at least one from among a change in the light detector parameter and a temperature change of the light detector according to the change in the light detector parameter, and a noise, and based on the analysis, adjusting at least one from among the light source parameter and the light detector parameter to minimize a system noise.

According to another aspect of an example embodiment, there is provided a spectrum measurement method of a spectrum measurement apparatus, the method including emitting light to a sample for calibration, receiving light, which is reflected or scattered from, or transmitted through the sample for calibration, and measuring an intensity of the received light, reconstructing a spectrum of the sample for calibration while adjusting a value of a spectrum reconstruction parameter, determining an optimal value of the spectrum reconstruction parameter based on a similarity between the reconstructed spectrum of the sample for calibration and an original spectrum of the sample for calibration, emitting light to a sample to be measured, receiving light, which is reflected or scattered from, or transmitted through the sample to be measured, and measuring an intensity of the received light, and reconstructing a spectrum of the sample for calibration corresponding to the determined optimal value of the spectrum reconstruction parameter.

BRIEF DESCRIPTION OF THE DRAWINGS

The above and/or other aspects will become apparent and more readily appreciated from the following description of example embodiments, taken in conjunction with the accompanying drawings, in which.

DETAILED DESCRIPTION

Figure 1:
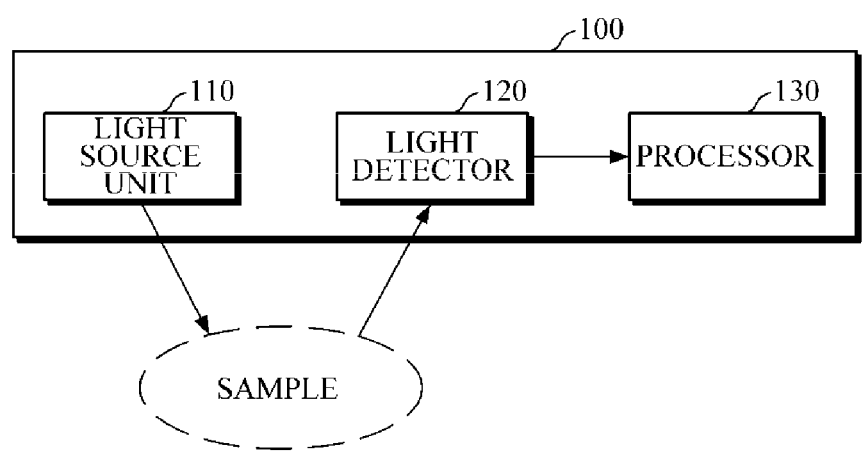
FIG. 1 is a block diagram illustrating an example of a spectrum measurement apparatus according to an example embodiment.

Hereinafter, example embodiments of the present disclosure will be described in detail with reference to the accompanying drawings. These example embodiments are described in sufficient detail to enable those skilled in the art to practice the present disclosure, and it is to be understood that the example embodiments are not intended to limit the present disclosure to particular modes of practice, and it is to be appreciated that all modification, equivalents, and alternatives that do not depart from the spirit and technical scope of the present disclosure are encompassed in the present disclosure. It should be noted that, in the drawings, the same reference symbols refer to same parts although illustrated in other drawings.

Process steps described herein may be performed differently from a specified order, unless the specified order is clearly stated in the context of the disclosure. For example, each step may be performed in a specified order, at substantially the same time, or in a reverse order.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Expressions such as "at least one from among," or "at least one of" when preceding a list of elements, modify the entire list of elements and do not modify the individual elements of the list.

Further, components that will be described in the specification are discriminated according to functions mainly performed by the components. That is, two or more components can be integrated into a single component. Furthermore, a single component can be separated into two or more components. Moreover, each component which will be described can additionally perform some or all of a function executed by another component n addition to the main function thereof. Some or all of the main function of each component which will be explained can be carried out by another component. Each component may be implemented as hardware, software, or a combination of both.

FIG. 1 is a block diagram illustrating an example of a spectrum measurement apparatus according to an example embodiment.

The spectrum measurement apparatus 100 is an apparatus for measuring a spectrum of a sample by optimizing a system parameter and/or a spectrum reconstruction parameter, and may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 1, the spectrum measurement apparatus 100 includes a light source unit 110, a light detector 120, and a processor 130.

The light source 110 may emit light to, for example, a sample for calibration and/or sample to be measured. The sample for calibration is a sample having a composition whose spectrum information is already known, and is used for calibration of the spectrum measurement apparatus 100; and the sample to be measured is a sample whose spectrum needs to be obtained and to analyze the composition thereof.

The light source unit 110 may include a plurality of light sources which emit light of different wavelengths to the samples. In an example embodiment, each light source may emit near infrared ray (NIR) or mid infrared ray (MIR) having different wavelength ranges. However, wavelengths of light emitted by the light sources y vary depending on the purpose of measurement or types of composition o be analyzed. Each light source may be configured as a single light emitting body, or may be configured as a group of a plurality of light emitting bodies. In an example embodiment, the light source may include a light emitting diode (LED), a laser diode, a fluorescent body, or the like, but example embodiments are not limited thereto.

In addition, the light source 110 may further include at least one optical element which directs light, emitted by each light source, toward a desired position of a sample.

The light detector 120 may receive light reflected or scattered from, or transmitted through the sample among the lights emitted by the light source unit 110, and may measure the intensity of the received light. In this case, the light detector 120 may amplify the received light according to a predetermined gain. In an example embodiment, the light detector 120 may include a photo diode, a photo transistor (PTr), a charge-coupled device (CCD), or the like. The light detector 120 may be configured as a single element, or may be an array having a plurality of elements.

There may be various numbers and arrangements of light sources, light detectors, and the like, and the number and arrangement thereof may vary depending on the types of a sample for analysis, the purpose of use, the size and shape of an electronic apparatus in which the spectrum measurement apparatus 100 is embedded, and the like.

The processor 130 may process various signals and operations related to the calibration of the spectrum measurement apparatus 100 and measurement of a spectrum of the sample to be measured.

The processor 130 may control the light source 110 and the light detector 120 according to a calibration period or a user's calibration command, and may perform calibration to optimize a system parameter and/or a spectrum reconstruction parameter. Here, various calibration periods may be set by a user. The system parameter may include a light source parameter, a light detector parameter, and the like. The light source parameter may include an operating frequency and a duty ratio of each light source, the size of an electric signal (voltage or current) applied to each light source. The light detector parameter may include an operating frequency of the light detector, an amplification gain in the optical detector, and the like. The spectrum reconstruction parameter is a parameter used for spectrum reconstruction based on an intensity of light measured by the light detector 120, and may be represented as a in the following Equation 1.

$$y_\alpha = (\alpha E + A^T A)^{-1} A^T p \qquad \text{[Equation 1]}$$

Here, α represents a spectrum reconstruction parameter, E represents a unit matrix, A represents a light spectrum, p represents an intensity measured by the light detector 120, and $y_\alpha$ represents a reconstructed spectrum. The light spectrum is a spectrum of light emitted by the light source 110, and information on the light spectrum may be pre-stored in an internal or external database.

Further, the processor 130 may obtain a spectrum of the sample to be measured by setting and controlling the light source 110 and the light detector 120 with an optimized system parameter according to a user's spectrum measurement command. In this case, the processor 130 may obtain the spectrum of the sample to be measured by reconstructing the spectrum using Equation 1 with an optimized spectrum reconstruction parameter α.

Figure 2:
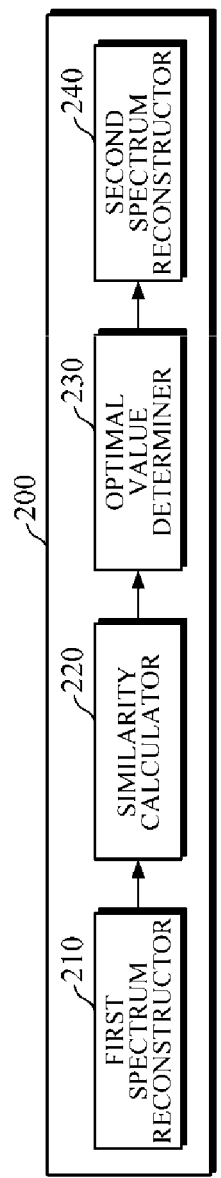
FIG. 2 is a block diagram illustrating an example of a processor according to an example embodiment.

FIG. 2 is a block diagram illustrating an example of a processor. The processor 200 of FIG. 2 may be an example of the processor 130 of FIG. 1.

Referring to FIG. 2, the processor 200 includes a first spectrum reconstructor 210, a similarity calculator 220, an optimal value determiner 230, and a second spectrum reconstructor 240.

Once the light detector 120 receives light, which is reflected or scattered from, or transmitted through the sample for calibration, and measures the intensity of the received light, the first spectrum reconstructor 210 may reconstruct the spectrum of the sample for calibration by using Equation 1 while adjusting a value of the spectrum reconstruction parameter α. In this case, the first spectrum reconstructor 210 may increase the value of the spectrum reconstruction parameter α between 0 and 0.1 by an increment of 0.01, which is exemplary and the value is not limited thereto. That is, a lower limit, an upper limit, and an increment of the value of the spectrum reconstruction parameter α may vary depending on the performance and usage of a system.

The similarity calculator 220 may calculate a similarity between a reconstructed spectrum of the sample for calibration, which is reconstructed for each value of the spectrum reconstruction parameter α, and an original spectrum of the sample for calibration. Here, the original spectrum of the sample for calibration is a spectrum of the sample for calibration which is fully reconstructed, and may be measured by a precise spectrometer. The information on the original spectrum of the sample for calibration may be pre-stored in an internal or external database.

In an example embodiment, the similarity calculator 220 may calculate the similarity between the reconstructed spectrum of the sample for calibration, which is reconstructed for each value of the spectrum reconstruction parameter α, and the original spectrum of the sample for calibration by using various similarity calculation methods, including Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The optimal value determiner 230 may determine an optimal value of the spectrum reconstruction parameter based on the similarity between the reconstructed spectrum of the sample for calibration, which is reconstructed for each value of the spectrum reconstruction parameter α, and the original spectrum of the sample for calibration. In an example embodiment, the optimal value determiner 230 may determine, as an optimal value, a value of the spectrum reconstruction parameter α at which the similarity between the reconstructed spectrum of the sample for calibration and the original spectrum of the sample for calibration is maximized.

Once the light detector 120 receives light, which is reflected or scattered from, or transmitted through the sample for calibration, and measures the intensity of the received light, the second spectrum reconstructor 240 may reconstruct the spectrum of the sample to be measured by using Equation 1 in which the optimal value of the spectrum reconstruction parameter α is reflected.

Figure 3:
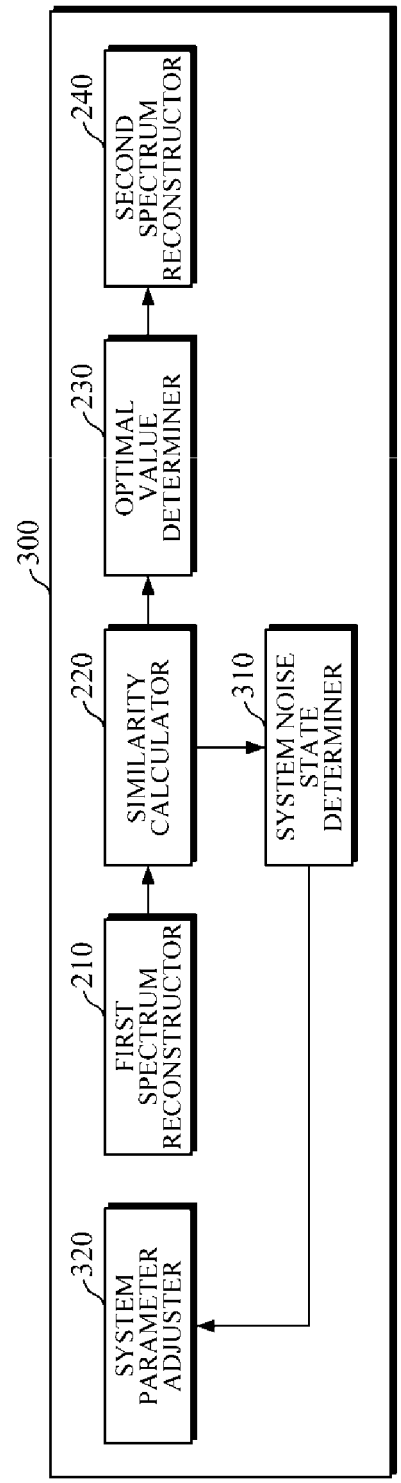
FIG. 3 is a block diagram illustrating an example of a processor according to an example embodiment.

FIG. 3 is a block diagram illustrating an example of a processor according to an example embodiment. The processor 300 of FIG. 3 may be an example of the processor 130 of FIG. 1.

Referring to FIG. 3, the processor 300 may include a first spectrum reconstructor 210, a similarity calculator 220, a system noise state determiner 310, a system parameter adjuster 320, an optimal value determiner 230, and a second spectrum reconstructor 240. Here, the first spectrum reconstructor 210, the similarity calculator 220, the optimal value determiner 230, and the second spectrum reconstructor 240 may be the same as those described above with reference to FIG. 2.

Based on the similarity, which is calculated by the similarity calculator 220 for each value of the spectrum reconstruction parameter α, between the reconstructed spectrum of the sample for calibration and the original spectrum of the sample for calibration, the system noise state determiner 310 may determine a system noise state which affects spectrum reconstruction.

In an example embodiment, the system noise state determiner 310 may determine a system noise state to be appropriate or inappropriate based on whether a change in the similarity between the reconstructed spectrum of the sample for calibration and the original spectrum of the sample for calibration, according to a change in the spectrum reconstruction parameter α, satisfies a predetermined condition. In this case, an appropriate system noise state indicates a state where the system noise is small enough to enable spectrum reconstruction to be performed effectively, and an inappropriate system noise state indicates a state where the system noise is too large to enable spectrum reconstruction to be performed effectively. In an example embodiment, the system noise state determiner 310 may determine the system noise state based on the number of maximum points of the change in the similarity between the reconstructed spectrum of the sample for calibration and the original spectrum of the sample for calibration according to a change in the spectrum reconstruction parameter α. For example, when the number of the maximum points of the change in the similarity is one, the system noise state determiner 330 may determine the system noise state to be appropriate, and when the number of the maximum points of the change in the similarity is zero or two or more, the system noise state determiner 330 may determine the system noise state to be inappropriate.

Once the system noise state being determined to be inappropriate, the system parameter adjuster 320 may adjust a system parameter. Here, as described above, the system parameter may include a light source parameter, a light detector parameter, and the like; the light source parameter may include an operating frequency and a duty ratio of each light source, the size of an electric signal (voltage or current) applied to each light source; and the light detector parameter may include an operating frequency of the light detector, an amplification gain in the optical detector, and the like.

Once the system noise state is determined to be appropriate, the optimal value determiner 230 may determine, as an optimal value, a value of the spectrum reconstruction parameter α at which the similarity between the reconstructed spectrum of the sample for calibration and the original spectrum of the sample for calibration is maximized.

Figure 4:
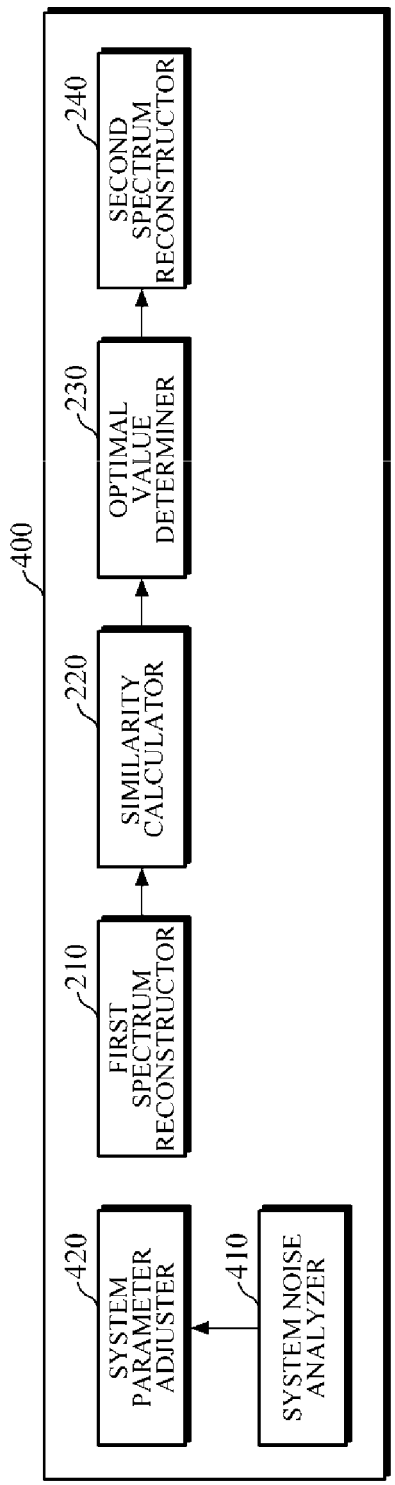
FIG. 4 is a block diagram illustrating an example of a processor according to an example embodiment.

FIG. 4 is a block diagram illustrating an example of a processor according to an example embodiment. The processor 400 of FIG. 4 may be an example of the processor 130 of FIG. 1.

Referring to FIG. 4, the processor 400 may include a system noise analyzer 410, a system parameter adjuster 420, a first spectrum reconstructor 210, a similarity calculator 220, an optimal value determiner 230, and a second spectrum reconstructor 240. Here, the first spectrum reconstructor 210, the similarity calculator 220, the optimal value determiner 230, and the second spectrum reconstructor 240 may be the same as those described above with reference to FIG. 2.

The system noise analyzer 410 may analyze a relationship between a change in the light source parameter (e.g., operating frequency, duty ratio, size of an electric signal applied to a light source, etc.) and/or a temperature change of the light source according to the change, and a noise. Further, the system noise analyzer 410 may analyze a relationship between a change in the light detector parameter (e.g., operating frequency, amplification gain, etc.) and/or a temperature change of the light detector according to the change, and a noise.

The system parameter adjuster 420 may adjust a system parameter to minimize a system noise based on the analysis of the system noise analyzer 410.

Once the system parameter is adjusted to minimize the system noise, and the light detector 120 receives light, which is reflected or scattered from or transmitted through the sample for calibration, and measures the intensity of the received light, the first spectrum reconstructor 210 may reconstruct the spectrum of the sample for calibration by using Equation 1 while adjusting a value of the spectrum reconstruction parameter α.

Figure 5:
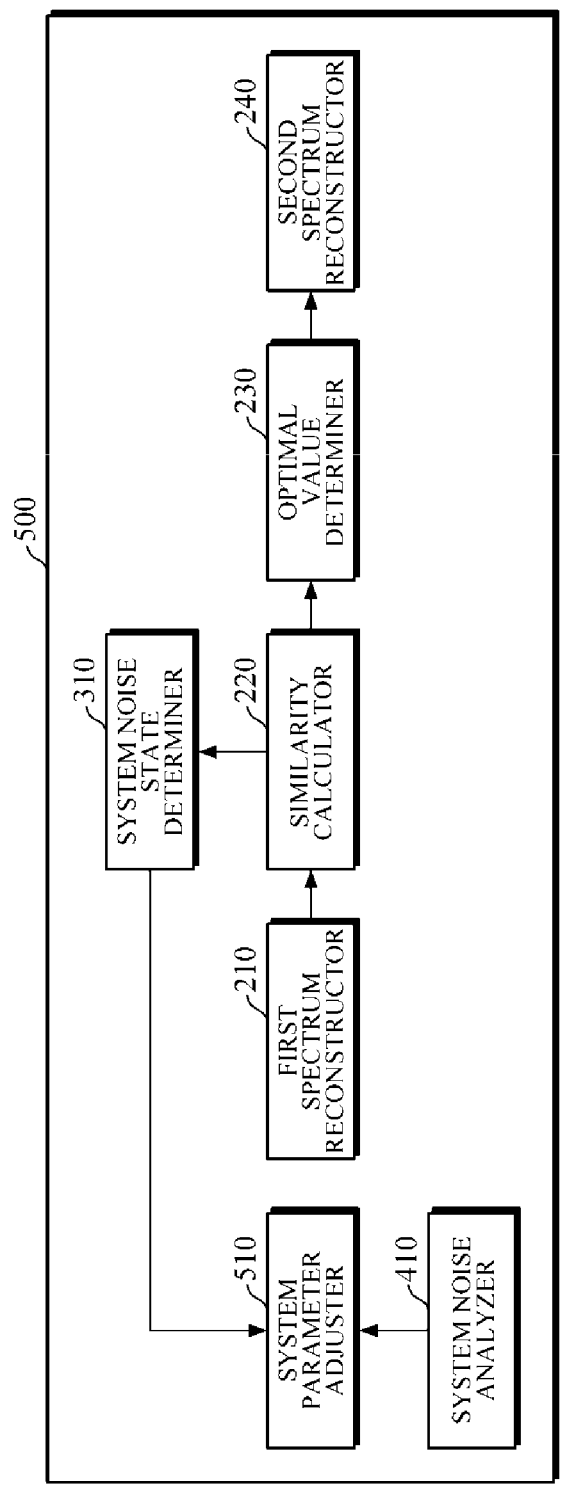
FIG. 5 is a block diagram illustrating an example of a processor according to an example embodiment.

FIG. 5 is a block diagram illustrating an example of a processor according to an example embodiment. The processor 500 of FIG. 5 may be an example of the processor 130 of FIG. 1.

Referring to FIG. 5, the processor 500 may include a system noise analyzer 410, a system parameter adjuster 510, a first spectrum reconstructor 210, a similarity calculator 220, a system noise state determiner 310, an optimal value determiner 230, and a second spectrum reconstructor 240. Here, the system noise analyzer 410, the first spectrum reconstructor 210, the similarity calculator 220, the system noise state determiner 310, the optimal value determiner 230, and the second spectrum reconstructor 240 may be the same as those described above with reference to FIG. 2 to FIG. 4.

The system parameter adjuster 510 may adjust a system parameter to minimize a system noise based on the analysis of the system noise analyzer 410. Further, when the system noise state is determined to be inappropriate based on the determination of the system noise state determiner 310, the system parameter adjuster 510 may adjust the system parameter.

Figure 6A:
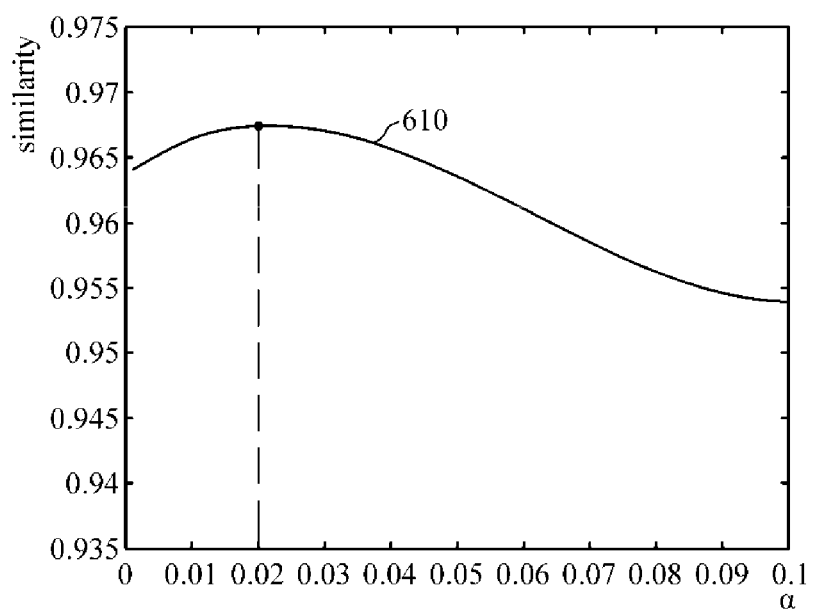
FIG. 6A and FIG. 6B are diagrams illustrating an example of change in a similarity between a reconstructed spectrum of a sample for calibration and an original spectrum of a sample for calibration according to a change in a spectrum reconstruction parameter according to an example embodiment.
Figure 6B:
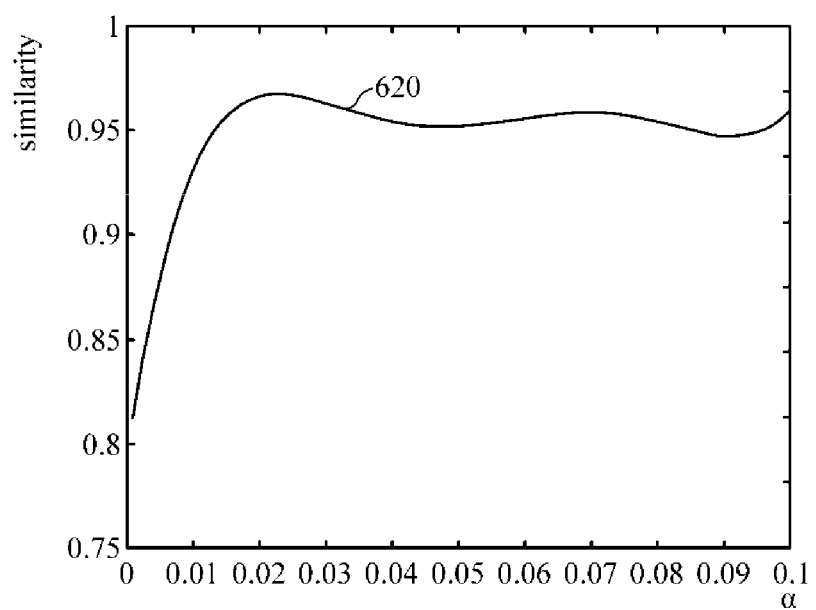

FIG. 6A and FIG. 6B are diagrams illustrating an example of change in a similarity between a reconstructed spectrum of a sample for calibration and an original spectrum of a sample for calibration according to a change in a spectrum reconstruction parameter. More specifically, FIG. 6A is an example of an appropriate system noise which affects spectrum reconstruction; and FIG. 6B is an example of an inappropriate system noise which affects spectrum reconstruction.

Referring to FIG. 3 and FIG. 6A, a change 610 of similarity between the reconstructed spectrum of the sample for calibration and the original spectrum of the sample for calibration according to a change in the spectrum reconstruction parameter α, has one maximum point, such that the spectrum noise state determiner 310 may determine that the system noise state affecting the spectrum reconstruction is appropriate. In this case, based on the change 610 of similarity according to the change in the spectrum reconstruction parameter α, the optimal value determiner 320 may determine a value of 0.02 to be an optimal value of the spectrum reconstruction parameter α, at which the similarity is maximized.

Referring to FIG. 3 and FIG. 6B, a change 620 of similarity between the reconstructed spectrum of the sample for calibration and the original spectrum of the sample for calibration according to a change in the spectrum reconstruction parameter α, has two maximum points, such that the spectrum noise state determiner 310 may determine that the system noise state affecting the spectrum reconstruction is inappropriate. In this case, the system parameter adjuster 320 may adjust the system parameter, and the first spectrum reconstructor 210 may reconstruct the spectrum of the sample for calibration by using Equation 1 while adjusting the value of the spectrum reconstruction parameter α based on a light intensity measured again by using the adjusted system parameter. Further, the similarity calculator 220 may calculate the similarity between the reconstructed spectrum of the sample for calibration, which is reconstructed for each value of the spectrum reconstruction parameter α, and the original spectrum of the sample for calibration. This process may be repeated until the spectrum noise state determiner 310 determines that the system noise, affecting the spectrum reconstruction, is appropriate.

Figure 7:
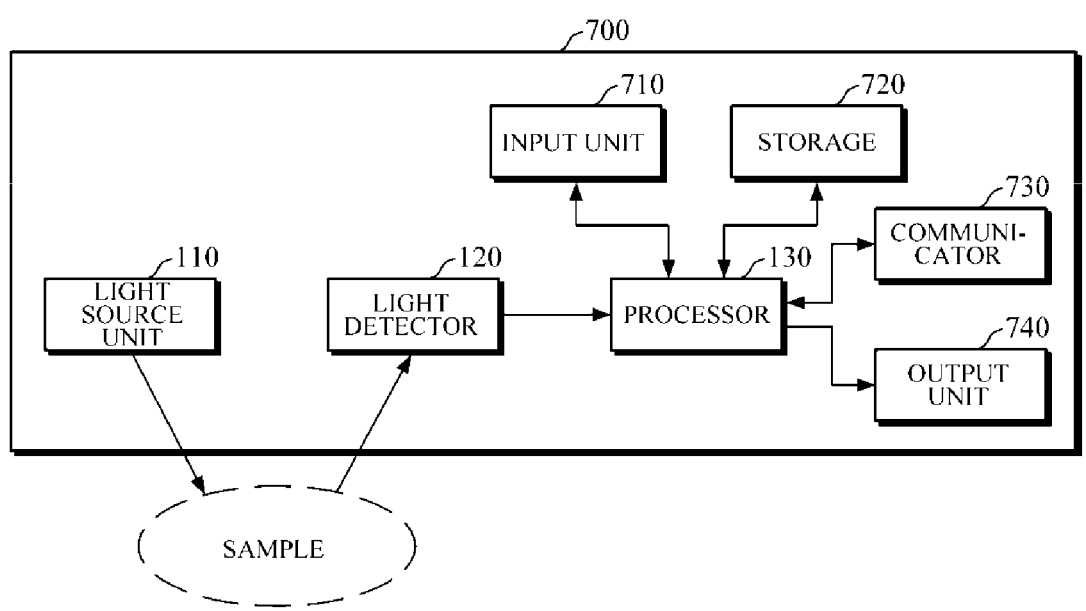
FIG. 7 is a block diagram illustrating an example of a spectrum measurement apparatus according to an example embodiment.

FIG. 7 is a block diagram illustrating an example of a spectrum measurement apparatus according to an example embodiment.

The spectrum measurement apparatus 700 may be embedded in an electronic apparatus. Examples of the electronic apparatus may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, a wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 7, the spectrum measurement apparatus 700 may include a light source unit 110, a light detector 120, a processor 130, an input unit 710, a storage 720, a communicator 730, and an output unit 740. Here, the light source unit 110, the light detector 120, and the processor 130 may be the same as those described above with reference to FIG. 1 to FIG. 5.

The input unit 710 may receive various operation signals from a user. In an example embodiment, the input unit 710 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage 720 may store programs or commands for operation of the spectrum measurement apparatus 700, and may store data input to and output from the spectrum measurement apparatus 700. Further, the storage 720 may store data of intensity of light measured by the light detector 120, data of the reconstructed spectrum and the determined optimal value of the spectrum reconstruction parameter by the processor 130, data of the original spectrum of the sample for calibration, data of the light spectrum, and the like.

The storage 720 may include at least one storage medium of a flash memory type memory, a hard disk type memory, a multimedia card micro type memory, a card type memory (e.g., an SD memory, an XD memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like. Further, the spectrum measurement apparatus 700 may operate an external storage medium, such as web storage and the like, which performs a storage function of the storage 720 on the Internet.

The communicator 730 may perform communication with an external device. For example, the communicator 730 may transmit, to the external device, data input by a user through the input unit 710, the data of intensity of light measured by the light detector 120, the data of the reconstructed spectrum and the determined optimal value of the spectrum reconstruction parameter by the processor 130, the data of the original spectrum of the sample for calibration, the data of the light spectrum, and the like; or the communicator 730 may receive various data, which may be useful for spectrum reconstruction or measurement, from the external device.

In this case, the external device may be a medical equipment using the data of intensity of light measured by the light detector 120, the data of the reconstructed spectrum and the determined optimal value of the spectrum reconstruction parameter by the processor 130, the data of the original spectrum of the sample for calibration, the data of the light spectrum, and the like, a printer to print out results, or a display device which displays the optimal value of the spectrum reconstruction parameter or the data of the reconstructed spectrum. In addition, examples of the external device may include a digital television (TV), a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 730 may communicate with an external device by using Bluetooth communication, Bluetooth Low Energy (BLE) communication, near field communication (NFC), wireless local area network (WLAN) communication, Zigbee communication, Infrared Data Association (IrDA) communication, Wi-Fi Direct (WFD) communication, ultra-wideband (UWB) communication, Ant+ communication, Wi-Fi communication, radio frequency identification (RFID) communication, 3G communication, 4G communication, 5G communication, and the like. However, this is exemplary and the communication is not limited thereto.

The output unit 740 may output the data of intensity of light measured by the light detector 120, the data of the reconstructed spectrum and the determined optimal value of the spectrum reconstruction parameter by the processor 130, the data of the original spectrum of the sample for calibration, data of the light spectrum, and the like. In an example embodiment, the output unit 740 may output the data of the reconstructed spectrum and the determined optimal value of the spectrum reconstruction parameter by the processor 130, the data of the original spectrum of the sample for calibration, data of the light spectrum, and the like, by using at least one of an acoustic method, a visual method, and a tactile method. The output unit 740 may include a display, a speaker, a vibrator, and the like.

Figure 8:
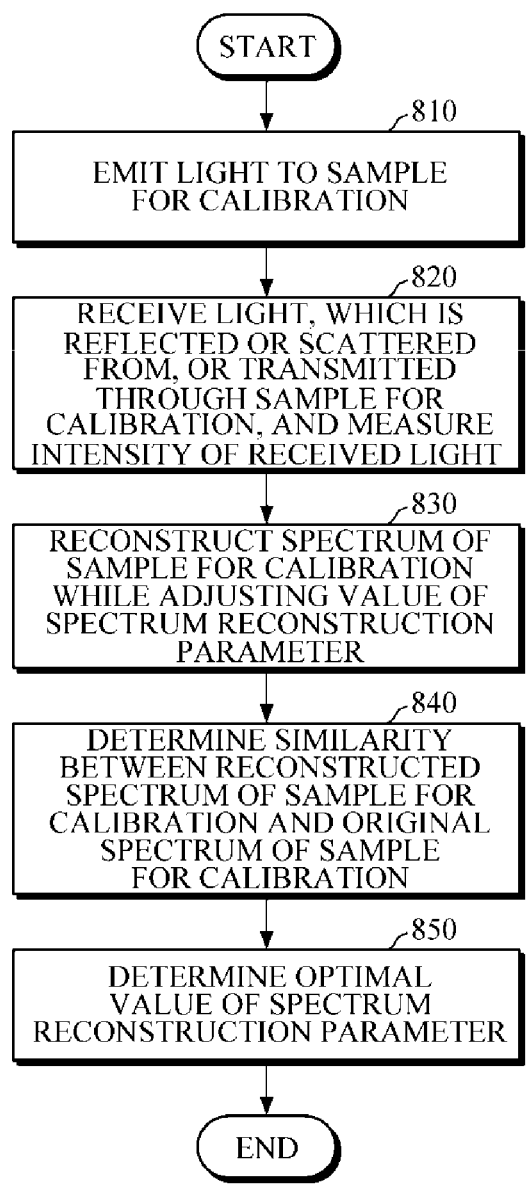
FIG. 8 is a flowchart illustrating an example of a calibration method of a spectrum measurement apparatus according to an example embodiment.

FIG. 8 is a flowchart illustrating an example of a calibration method of a spectrum measurement apparatus. The calibration method may be performed by the spectrum measurement apparatus 100 of FIG. 1.

Referring to FIG. 1 and FIG. 8, the spectrum measurement apparatus 100 may emit light to the sample for calibration in 810, and may receive light, which is reflected or scattered from, or transmitted through the sample for calibration, and may measure the intensity of the received light in 820.

Upon measuring the intensity of the received light, the spectrum measurement apparatus 100 may reconstruct a spectrum of the sample for calibration by using Equation 1 while adjusting a value of the spectrum reconstruction parameter α in 830.

The spectrum measurement apparatus 100 may calculate a similarity between the reconstructed spectrum of the sample for calibration, which is reconstructed for each value of the spectrum reconstruction parameter α, and the original spectrum of the sample for calibration in 840. In an example embodiment, the spectrum measurement apparatus 100 may calculate the similarity between the reconstructed spectrum of the sample for calibration, which is reconstructed for each value of the spectrum reconstruction parameter α, and the original spectrum of the sample for calibration by using various similarity calculation methods, including Euclidean distance, Manhattan Distance, Cosine Distance, Mahalanobis Distance, Jaccard Coefficient, Extended Jaccard Coefficient, Pearson's Correlation Coefficient, Spearman's Correlation Coefficient, and the like.

The spectrum measurement apparatus 100 may determine an optimal value of the spectrum reconstruction parameter α based on the similarity between the reconstructed spectrum of the sample for calibration, which is reconstructed for each value of the spectrum reconstruction parameter α, and the original spectrum of the sample for calibration in 850. In an example embodiment, the spectrum measurement apparatus 100 may determine, as an optimal value, a value of the spectrum reconstruction parameter α at which the similarity between the reconstructed spectrum of the sample for calibration and the original spectrum of the sample for calibration is maximized.

Figure 9:
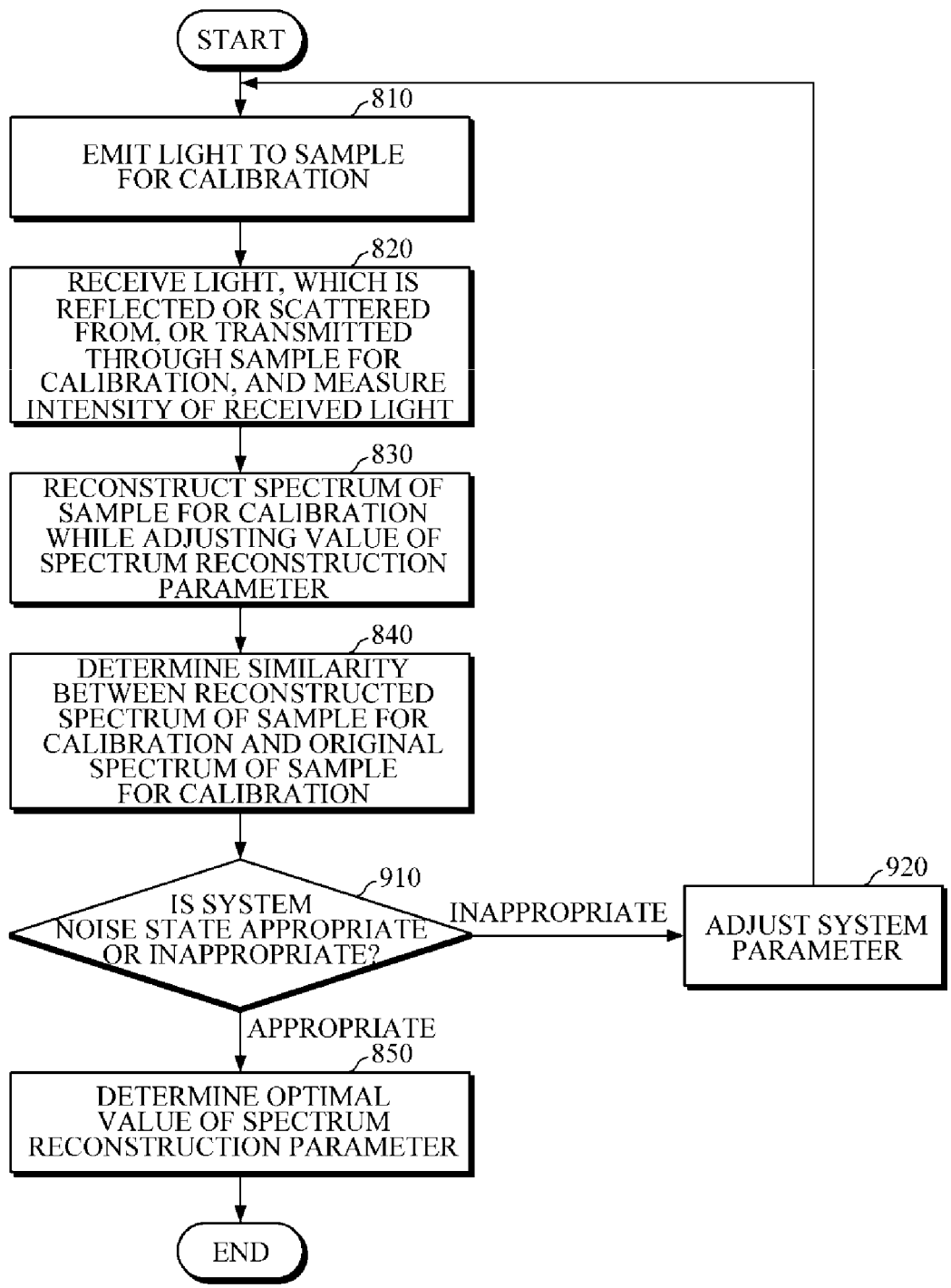
FIG. 9 is a flowchart illustrating an example of a calibration method of a spectrum measurement apparatus according to an example embodiment.

FIG. 9 is a flowchart illustrating an example of a calibration method of a spectrum measurement apparatus according to an example embodiment. The calibration method of FIG. 9 may be performed by the spectrum measurement apparatus 100 of FIG. 1.

Referring to FIG. 1 and FIG. 9, the spectrum measurement apparatus 100 may emit light to the sample for calibration in 810, and may receive light, which is reflected or scattered from, or transmitted through the sample for calibration, and may measure the intensity of the received light in 820.

Upon measuring the intensity of the received light, the spectrum measurement apparatus 100 may reconstruct a spectrum of the sample for calibration by using Equation 1 while adjusting a value of the spectrum reconstruction parameter α in 830.

The spectrum measurement apparatus 100 may calculate a similarity between the reconstructed spectrum of the sample for calibration, which is reconstructed for each value of the spectrum reconstruction parameter α, and the original spectrum of the sample for calibration in 840.

The spectrum measurement apparatus 100 may determine a system noise state, which affects spectrum reconstruction, based on the similarity between the reconstructed spectrum of the sample for calibration, which is reconstructed for each value of the spectrum reconstruction parameter α, and the original spectrum of the sample for calibration in 910. In an example embodiment, the spectrum measurement apparatus 100 may determine a system noise state to be appropriate or inappropriate based on whether a change in the similarity between the reconstructed spectrum of the sample for calibration and the original spectrum of the sample for calibration, according to a change in the spectrum reconstruction parameter α, satisfies a predetermined condition. For example, when the number of maximum points of the change in the similarity according to the change in the spectrum reconstruction parameter α is one, the spectrum measurement apparatus 100 may determine the system noise state to be appropriate, and when the number of the maximum points of the change in the similarity according to the change in the spectrum reconstruction parameter α is zero or two or more, the spectrum measurement apparatus 100 may determine the system noise state to be inappropriate.

Once the system noise state is determined to be inappropriate, the spectrum measurement apparatus 100 may adjust a system parameter in 920 and may return to the operation 810 to emit light to the sample for calibration.

Once the system noise state is determined to be appropriate, the spectrum measurement apparatus 100 may determine an optimal value of the spectrum reconstruction parameter α based on the similarity between the reconstructed spectrum of the sample for calibration, which is reconstructed for each value of the spectrum reconstruction parameter α, and the original spectrum of the sample for calibration in 850.

Figure 10:
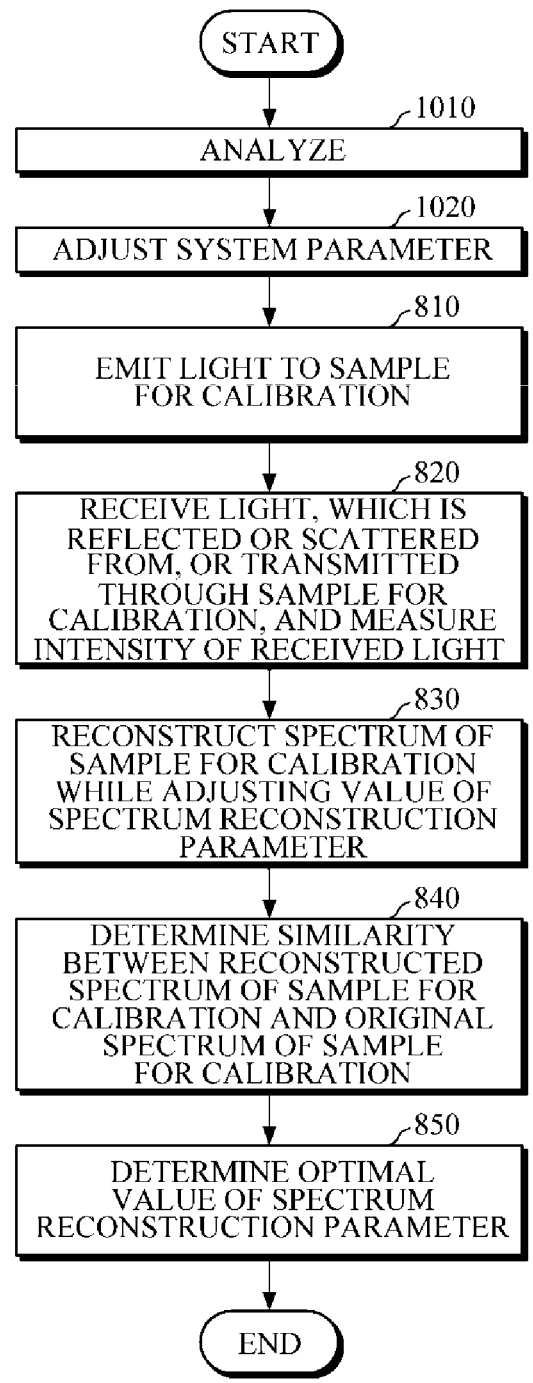
FIG. 10 is a flowchart illustrating an example of a calibration method of a spectrum measurement apparatus according to an example embodiment.

FIG. 10 is a flowchart illustrating an example of a calibration method of a spectrum measurement apparatus according to an example embodiment. The calibration method of FIG. 10 may be performed by the spectrum measurement apparatus 100 of FIG. 1.

Referring to FIG. 1 and FIG. 10, the spectrum measurement apparatus 100 may analyze a relationship between a change in the light source parameter (e.g., operating frequency, duty ratio, size of an electric signal applied to a light source, etc.) and/or a temperature change of the light source according to the change, and a noise. Further, the spectrum measurement apparatus 100 may analyze a relationship between a change in the light detector parameter (e.g., operating frequency, amplification gain, etc.) and/or a temperature change of the light detector according to the change, and a noise in 1010.

The spectrum measurement apparatus 100 may adjust a system parameter in 1020 based on the analysis in 1010 to minimize a system noise.

The spectrum measurement apparatus 100 may emit light to the sample for calibration in 810; and may receive light, which is reflected or scattered from, or transmitted through the sample for calibration, and may measure the intensity of the received light in 820.

Upon measuring the intensity of the received light, the spectrum measurement apparatus 100 may reconstruct a spectrum of the sample for calibration by using Equation 1 while adjusting a value of the spectrum reconstruction parameter α in 830.

The spectrum measurement apparatus 100 may calculate a similarity between the reconstructed spectrum of the sample for calibration, which is reconstructed for each value of the spectrum reconstruction parameter α, and the original spectrum of the sample for calibration in 840.

The spectrum measurement apparatus 100 may determine an optimal value of the spectrum reconstruction parameter α based on the similarity between the reconstructed spectrum of the sample for calibration, which is reconstructed for each value of the spectrum reconstruction parameter α, and the original spectrum of the sample for calibration in 850.

Figure 11:
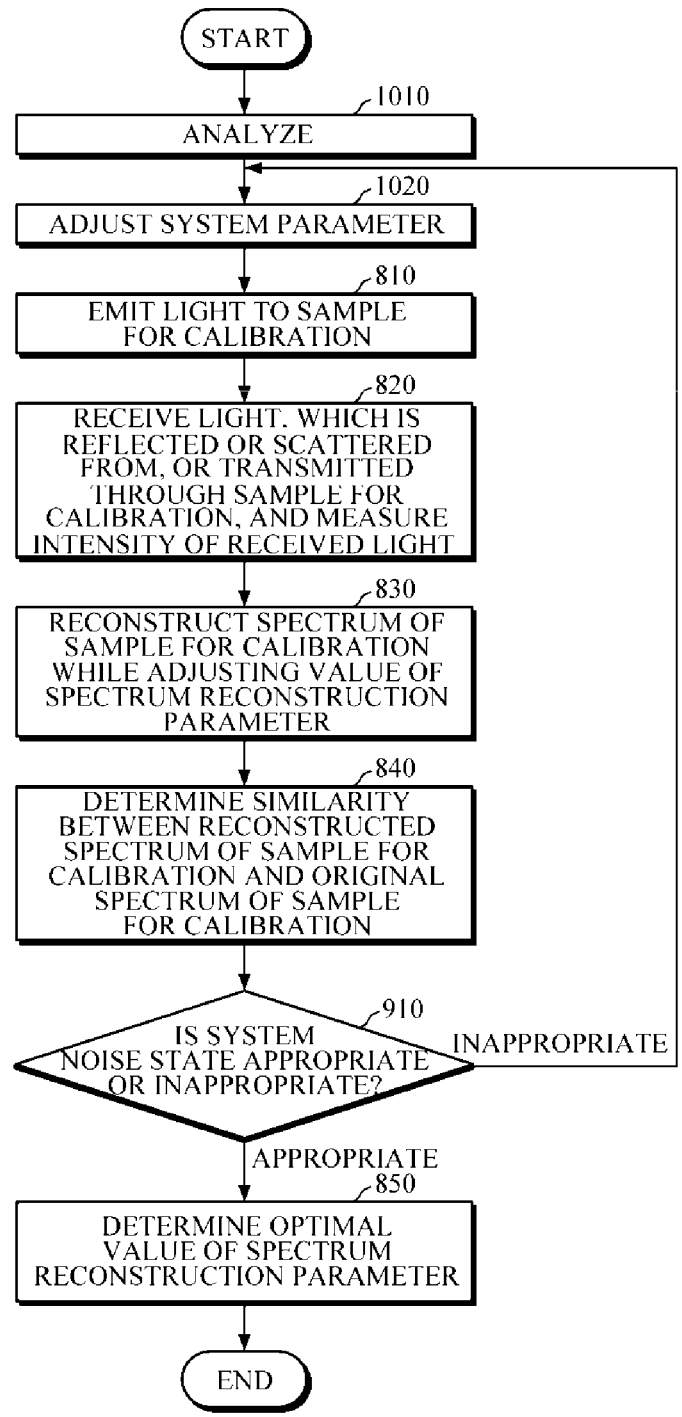
FIG. 11 is a flowchart illustrating an example of a calibration method of a spectrum measurement apparatus according to an example embodiment.

FIG. 11 is a flowchart illustrating an example of a calibration method of a spectrum measurement apparatus according to an example embodiment. The calibration method of FIG. 11 may be performed by the spectrum measurement apparatus 100 of FIG. 1.

Referring to FIG. 1 and FIG. 11, the spectrum measurement apparatus 100 may analyze a relationship between a change in the light source parameter (e.g., operating frequency, duty ratio, size of an electric signal applied to a light source, etc.) and/or a temperature change of the light source according to the change, and a noise. Further, the spectrum measurement apparatus 100 may analyze a relationship between a change in the light detector parameter (e.g., operating frequency, amplification gain, etc.) and/or a temperature change of the light detector according to the change, and a noise in 1010.

The spectrum measurement apparatus 100 may adjust a system parameter in 1020 based on the analysis in 1010 to minimize a system noise.

The spectrum measurement apparatus 100 may emit light to the sample for calibration in 810; and may receive light, which is reflected or scattered from, or transmitted through the sample for calibration, and may measure the intensity of the received light in 820.

Upon measuring the intensity of the received light, the spectrum measurement apparatus 100 may reconstruct a spectrum of the sample for calibration by using Equation 1 while adjusting a value of the spectrum reconstruction parameter α in 830.

The spectrum measurement apparatus 100 may calculate a similarity between the reconstructed spectrum of the sample for calibration, which is reconstructed for each value of the spectrum reconstruction parameter α, and the original spectrum of the sample for calibration in 840.

The spectrum measurement apparatus 100 may determine a system noise state, which affects spectrum reconstruction, based on the similarity between the reconstructed spectrum of the sample for calibration, which is reconstructed for each value of the spectrum reconstruction parameter α, and the original spectrum of the sample for calibration in 910.

Once the system noise state is determined to be inappropriate, the spectrum measurement apparatus 100 may return to the operation 1020 to adjust a system parameter.

Once the system noise state is determined to be appropriate, the spectrum measurement apparatus 100 may determine an optimal value of the spectrum reconstruction parameter α based on the similarity between the reconstructed spectrum of the sample for calibration, which is reconstructed for each value of the spectrum reconstruction parameter α, and the original spectrum of the sample for calibration in 850.

Figure 12:
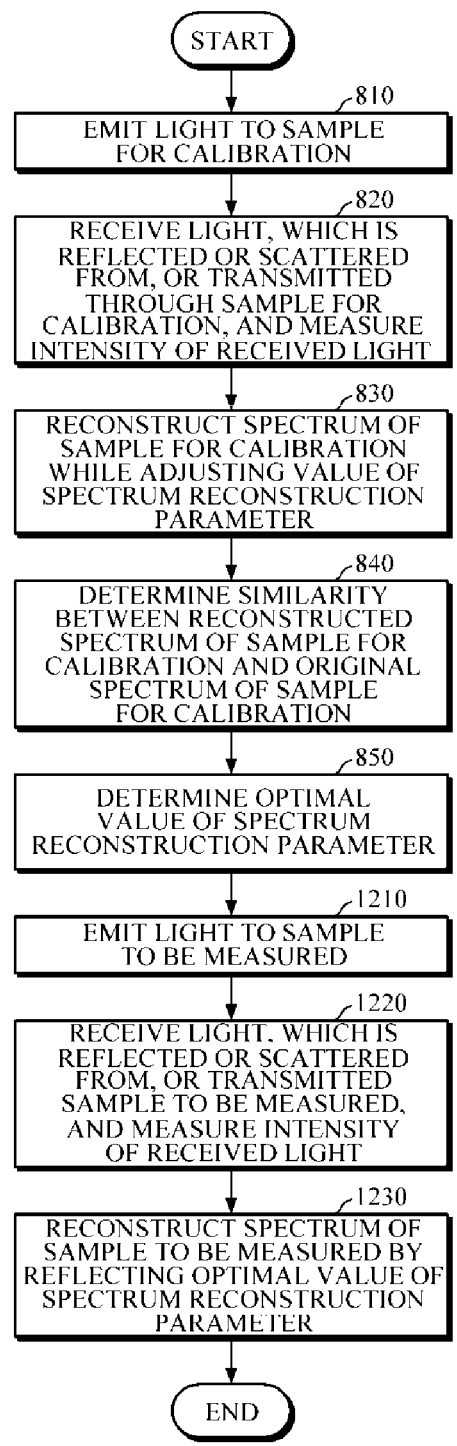
FIG. 12 is a flowchart illustrating an example of a spectrum measurement method according to an example embodiment.

FIG. 12 is a flowchart illustrating an example of a spectrum measurement method according to an example embodiment. The spectrum measurement method of FIG. 12 may be performed by the spectrum measurement apparatus 100 of FIG. 1.

Referring to FIG. 1 and FIG. 12, the spectrum measurement apparatus 100 may emit light to the sample for calibration in 810; and may receive light, which is reflected or scattered from, or transmitted through the sample for calibration, and may measure the intensity of the received light in 820.

Upon measuring the intensity of the received light, the spectrum measurement apparatus 100 may reconstruct a spectrum of the sample for calibration by using Equation 1 while adjusting a value of the spectrum reconstruction parameter α in 830.

The spectrum measurement apparatus 100 may calculate a similarity between the reconstructed spectrum of the sample for calibration, which is reconstructed for each value of the spectrum reconstruction parameter α, and the original spectrum of the sample for calibration in 840.

The spectrum measurement apparatus 100 may determine an optimal value of the spectrum reconstruction parameter α based on the similarity between the reconstructed spectrum of the sample for calibration, which is reconstructed for each value of the spectrum reconstruction parameter α, and the original spectrum of the sample for calibration in 850.

The spectrum measurement method 100 may emit light to the sample to be measured in 1210; and may receive light, which is reflected or scattered from, or transmitted through the sample to be measured, and may measure the intensity of the received light in 1220.

The spectrum measurement method 100 may reconstruct the spectrum of the sample to be measured by using Equation 1 in which the optimal value of the spectrum reconstruction parameter α is reflected in 1230.

The present disclosure can be realized as a computer-readable code written on a computer-readable recording medium. Codes and code segments needed for realizing the present disclosure can be deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

While example embodiments have been described with reference to the drawings, it will be understood by those of ordinary skill in the art that various changes in form and details may be made therein without departing from the spirit and scope as defined by the following claims and their equivalents.

What is claimed is:

1. A spectrum measurement apparatus comprising:
a light source configured to emit light to a sample;
a light detector configured to receive light, which is reflected or scattered from, or transmitted through the sample, and to measure an intensity of the received light; and
a processor configured to reconstruct a spectrum of the sample for calibration while adjusting a value of a spectrum reconstruction parameter in response to the light detector receiving the light and measuring the intensity of the received light, and to determine an optimal value of the spectrum reconstruction parameter based on a similarity between the reconstructed spectrum of the sample for calibration and an original spectrum of the sample for calibration.

2. The spectrum measurement apparatus of claim 1, wherein the processor is further configured to calculate the similarity between the reconstructed spectrum of the sample for calibration and the original spectrum of the sample for calibration by using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

3. The spectrum measurement apparatus of claim 1, wherein the processor is further configured to determine, as the optimal value of the spectrum reconstruction parameter, a value of the spectrum reconstruction parameter at which the similarity between the reconstructed spectrum of the sample for calibration and the original spectrum of the sample for calibration is maximized.

4. The spectrum measurement apparatus of claim 1, wherein in response to the light detector receiving the light and measuring the intensity of the received light, the processor is further configured to reconstruct a spectrum of the sample corresponding to the determined optimal value of the spectrum reconstruction parameter.

5. The spectrum measurement apparatus of claim 1, wherein the processor is further configured to determine a system noise state, which affects spectrum reconstruction, based on a change in the similarity between the reconstructed spectrum of the sample for calibration and the original spectrum of the sample for calibration according to a change in the spectrum reconstruction parameter.

6. The spectrum measurement apparatus of claim 5, wherein the processor is further configured to determine the system noise state based on a number of maximum points of the change in the similarity according to the change in the spectrum reconstruction parameter.

7. The spectrum measurement apparatus of claim 6, wherein in response to the number of the maximum points being one, the processor is further configured to determine the system noise state to be an appropriate state, and in response to the number of the maximum points not being one, the processor is further configured to determine the system noise state to be an inappropriate state.

8. The spectrum measurement apparatus of claim 7, wherein in response to determination of the system noise state to be in the inappropriate state, the processor is further configured to adjust a system parameter.

9. The spectrum measurement apparatus of claim 8, wherein the system parameter comprises at least one from among a light source parameter and a light detector parameter,
wherein the light source parameter comprises at least one from among an operating frequency and a duty ratio of the light source, and a size of an electric signal applied to the light source; and
the light detector parameter comprises at least one from among an operating frequency and an amplification gain of the light detector.

10. The spectrum measurement apparatus of claim 9, wherein the processor is further configured to analyze:
a relationship between at least one from among a change in the light source parameter and a temperature change of the light source according to the change in the light source parameter, and a noise; and
a relationship between at least one from among a change in the light detector parameter and a temperature change of the light detector according to the change in the light detector parameter, and a noise,
wherein based on the analysis, the processor is further configured to adjust at least one from among the light source parameter and the light detector parameter to minimize a system noise.

11. A calibration method of a spectrum measurement apparatus, the method comprising:
emitting light to a sample for calibration;
receiving light, which is reflected or scattered from, or transmitted through the sample for calibration, and measuring an intensity of the received light;
in response to measuring the intensity of the received light, reconstructing a spectrum of the sample for calibration while adjusting a value of a spectrum reconstruction parameter;
determining a similarity between the reconstructed spectrum of the sample for calibration and an original spectrum of the sample for calibration; and
determining an optimal value of the spectrum reconstruction parameter based on the determined similarity.

12. The method of claim 11, wherein the determining of the similarity comprises using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

13. The method of claim 11, wherein the determining of the optimal value of the spectrum reconstruction parameter comprises determining, as the optimal value of the spectrum reconstruction parameter, a value of the spectrum reconstruction parameter at which the similarity between the reconstructed spectrum of the sample for calibration and the original spectrum of the sample for calibration is maximized.

14. The method of claim 11, further comprising determining a system noise state, which affects spectrum reconstruction, based on a change in the similarity between the reconstructed spectrum of the sample for calibration and the original spectrum of the sample for calibration according to a change in the spectrum reconstruction parameter.

15. The method of claim 14, wherein the determining of the system noise state comprises determining the system noise state based on a number of maximum points of the change in the similarity according to the change in the spectrum reconstruction parameter.

16. The method of claim 15, wherein the determining of the system noise state comprises, in response to the number of the maximum points being one, determining the system noise state to be in an appropriate state, and in response to the number of the maximum points not being one, determining the system noise state to be in an inappropriate state.

17. The method of claim 16, further comprising, in response to determination of the system noise state to be in the inappropriate state, adjusting a system parameter.

18. The method of claim 17, wherein the system parameter comprises at least one from among a light source parameter and a light detector parameter,
   wherein the light source parameter comprises at least one from among an operating frequency and a duty ratio of a light source unit, and a size of an electric signal applied to the light source unit; and
   the light detector parameter comprises at least one from among an operating frequency and an amplification gain of a light detector.

19. The method of claim 18, further comprising:
analyzing a relationship between at least one from among a change in the light source parameter and a temperature change of the light source unit according to the change in the light source parameter, and a noise;
   analyzing a relationship between at least one from among a change in the light detector parameter and a temperature change of the light detector according to the change in the light detector parameter, and a noise; and
   based on the analysis, adjusting at least one from among the light source parameter and the light detector parameter to minimize a system noise.

20. A spectrum measurement method of a spectrum measurement apparatus, the method comprising:
   emitting light to a sample for calibration;
   receiving light, which is reflected or scattered from, or transmitted through the sample for calibration, and measuring an intensity of the received light;
   reconstructing a spectrum of the sample for calibration while adjusting a value of a spectrum reconstruction parameter;
   determining an optimal value of the spectrum reconstruction parameter based on a similarity between the reconstructed spectrum of the sample for calibration and an original spectrum of the sample for calibration;
   emitting light to a sample to be measured;
   receiving light, which is reflected or scattered from, or transmitted through the sample to be measured, and measuring an intensity of the received light; and
   reconstructing a spectrum of the sample for calibration corresponding to the determined optimal value of the spectrum reconstruction parameter.

* * * * *